July 15, 1969 H. G. FRITSCHER Plant Pat. 2,904
GLADIOLUS PLANT
Filed Nov. 24, 1967
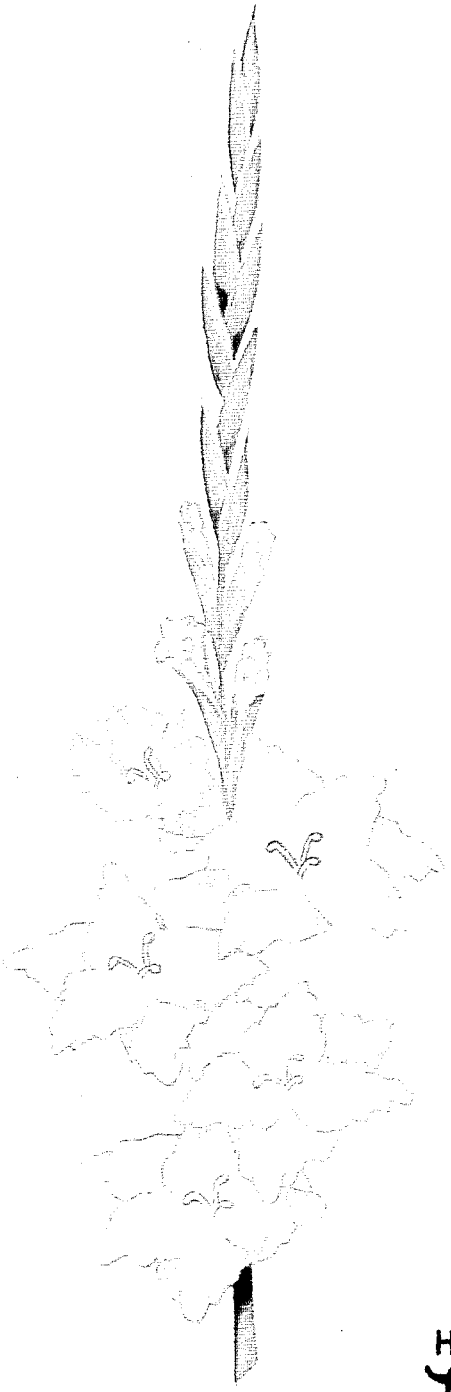
INVENTOR
Henry G. Fritscher
By: Lamont Johnston
ATTORNEY

United States Patent Office

Plant Pat. 2,904
Patented July 15, 1969

2,904

GLADIOLUS PLANT

Henry G. Fritscher, Santa Rosa, Calif., assignor to Selected Glads, Inc., New Albany, Ind., a corporation of Tennessee

Filed Nov. 24, 1967, Ser. No. 685,718
Int. Cl. A01h *5/02*
U.S. Cl. Plt.—85 1 Claim

My invention relates to a new and improved variety of gladiolus plant and is notable particularly for the pure white color of its blossom, extremely good health, vigor and ability to perform well in all parts of the United States.

To the best of my knowledge, this variety is the result of a cross between Snow Cloud (unpatented) and an unnamed white seedling (unpatented). The unnamed white seedling was the pollen parent and Snow Cloud the seed parent. Hand cross pollination was done by me in my field at Sebastopol, Calif., but no precaution was taken to prevent admixture by bees or insects.

This new variety has been asexually reproduced by me in California by natural increase from cormels through several generations and its characteristics have proven to be permanently fixed.

The illustration, made a part of this application, shows a single bloom spike, reduced in size. The illustration shows the form and placement of the florets on the spike and is as nearly true to color as it is possible to depict. In the following detailed description the ordinary dictionary meanings of color terms are intended.

The plant

Growth: Strong; attains a height of 70 inches overall. Fine propagator.

Blooming: Blooms in 85 days from large bulbs in the North.

Stems: Diameter of stem is ½ inch. Color of stem above bulb is light pink.

Foliage: Deep green and semi-drooping. Leaves are 1½ to 1¾ inches across.

Disease resistance: Extremely resistant to known gladiolus diseases.

Corms: Round and high-crowned, with excellent husk coverage. Husk has a pink cast. Color of flesh is yellow.

The flower

Spike: Flowerhead is 23 inches high, with 18 to 20 buds of which 7 open at one time.

Bud:

*Size.*—Opening buds are 4 inches long.

*Opening.*—5 to 6 show color at one time.

Flower: Florets are formally placed on the spike. Individual florets are 5½ inches across. The form is slightly ruffled and triangular. The keeping qualities are excellent.

Petals: The shape is frilled and rounded. Upper petals are 2¾ inches across; lip, 1¾ inches. The substance is firm. There is no fragrance. Color—pure white with a slight creamy cast deep in the throat. Stamens are edged purple; the pistil is white.

Comparisons

My new variety resembles Icicle (unpatented), but differs as follows:

Color is whiter and purer. Florets are more precisely formed and petals are more ruffled. The blossom size is much larger. Health, vigor and propagation are superior.

Having thus disclosed my invention, I claim:

1. The new and improved variety of gladiolus plant, substantially as herein shown and described, characterized by its vigor, extremely good health, pure white color of its blossom and consistent performance in all parts of the United States.

No references cited.

ROBERT E. BAGWILL, Primary Examiner